United States Patent
Schelhaas et al.

(10) Patent No.: US 6,437,180 B1
(45) Date of Patent: Aug. 20, 2002

(54) PREPARATION OF ALIPHATIC α, ω-DICARBOXYLIC ACIDS

(75) Inventors: Michael Schelhaas, Köln (DE); Helmut Greiving, Upper St. Clair, PA (US); Manfred Jautelat, Burscheid (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/568,894

(22) Filed: May 11, 2000

(30) Foreign Application Priority Data

May 18, 1999 (DE) .......................... 199 22 643

(51) Int. Cl.$^7$ .......................... C07C 51/16; C07C 55/00
(52) U.S. Cl. .......................... 562/542; 562/544; 562/590
(58) Field of Search ................. 562/544, 545, 562/542, 590

(56) References Cited

U.S. PATENT DOCUMENTS

| 4,259,520 A | | 3/1981 | Kummer et al. ............ 560/204 |
| 4,532,079 A | * | 7/1985 | Venturello et al. .......... 260/413 |
| 5,321,158 A | * | 6/1994 | Warwel et al. .............. 562/544 |
| 5,336,793 A | | 8/1994 | Gardano et al. ............ 554/138 |

FOREIGN PATENT DOCUMENTS

WO   WO-95/00243   *   1/1995

OTHER PUBLICATIONS

Chem. Lett. (month unavailable) 1989, pp. 857–860, T. Oguchi et al, Oxidative Cleavage of Olefins into Carboxylic Acids with Hydrogen Peroxide by Tungstic Acid.

J. Org. Chem. 63, Oct. 16, 1998, pp. 7190–7206, Ermanno Antonelli et al, Efficient Oxidative Cleavage of Olefins to Carboxylic Acids with Hydrogen Peroxide Catalyzed by Methyltrioctylammonium Tetrakis(oxodiperoxotungsto)phosphate(3–) under Two–Phase Conditions. Synthetic Aspects and Investigation of the Reaction Course.

* cited by examiner

Primary Examiner—James O. Wilson
Assistant Examiner—Zachary Tucker
(74) Attorney, Agent, or Firm—Joseph C. Gil; Diderico van Eyl

(57) ABSTRACT

A process for preparing aliphatic $C_{4-18}$ α,ω-dicarboxylic acids by oxidation of $C_{6-20}$ α,ω-dienes with hydrogen peroxide or compounds which release hydrogen peroxide under the reaction conditions as is characterized in that the reaction is carried out in the presence of a transition metal catalyst of group VI and of a mixture containing at least one organic acid and one aprotic organic solvent. A specific temperature profile is maintained at different phases of the reaction, which increases yield and selectivity.

10 Claims, No Drawings

PREPARATION OF ALIPHATIC α, ω-DICARBOXYLIC ACIDS

BACKGROUND OF THE INVENTION

The present invention relates to a process for preparing aliphatic $C_4$–$C_{18}$ α,ω-dicarboxylic acids from $C_6$–$C_{20}$ α,ω-dienes.

Aliphatic α,ω-dicarboxylic acids are important compounds in organic synthesis because of their bifunctionality. The short-chain representatives are important reagents for organic syntheses of all kinds, while the longer-chain representatives are preferred for making polyamides, polyesters, plasticizers, alkyd resins and lubricants.

Special significance attaches to adipic acid, an important starting material for making nylon 66.

In industry, adipic acid is produced from cyclohexane in a two-step process. First, the cyclohexane is oxidized to a cyclohexanol-cyclo-hexanone mixture. This so-called "KA oil" is further oxidized, generally with nitric acid, producing stoichiometric amounts of nitrous gases. The alternative use of atmospheric oxygen as oxidizing agent results in lower product selectivity.

A further process for producing adipic acid is the biscarbonylation of butadiene (U.S. Pat. No. 4,259,520), which leads to adipic acid via the hydrolysis of the bisester. The formation of isomeric methyl glutarate, the branched biscarbonylation product, is unavoidable.

Adipic acid has been prepared from cyclohexene using tungstic acid/aqueous hydrogen peroxide solution in tert-butanol. The main disadvantage here was the long reaction time of 24 hours (see T. Oguchi et al., Chem. Lett. 1989, 857–860).

It is an object of the present invention to provide easy and selective access to adipic acid via α,ω-dienes as readily available reactants.

It is known that α,ω-dicarboxylic acids can be prepared by oxidative cracking of α,ω-dienes or cyclic alkenes. The oxidizing agents used are ozone, potassium permanganate, chromates or peroxides.

Antonelli et al., J. Org. Chem. 63, 1998, 7190–7206 describe the conversion of 1,7-octadiene into adipic acid in the presence of aqueous hydrogen peroxide solution and methyltrioctylammonium tetrakis-(oxodiperoxotungsten) phosphate as phase transfer catalyst. This process, however, provided an adipic acid yield of only 60%.

DESCRIPTION OF THE INVENTION

The stated object of the invention is achieved by such a process for preparing optionally substituted aliphatic $C_4$–$C_8$ α,ω-dicarboxylic acids by oxidation of optionally substituted $C_6$–$C_{20}$ α,ω-dienes with hydrogen peroxide or compounds which release hydrogen peroxide under the reaction conditions as is characterized in that the reaction is carried out in the presence of transition metal catalysts of group VI and of a mixture comprising at least one organic acid and at least one aprotic organic solvent. The process of the invention can also be used to produce adipic acid. The process of the invention is notable for providing the desired reaction products selectively and in very high yields within short reaction times.

In a preferred embodiment of the process according to the invention, the organic acids used are straight-chain or branched $C_2$–$C_8$ alkylcarboxylic acids, $C_6$–$C_{14}$ arylcarboxylic acids or $C_7$–$C_{15}$ arylalkyl-carboxylic acids which optionally bear at least one further substituent selected from the group consisting of halogen atoms, straight-chain or branched $C_1$–$C_6$ alkyl groups, $C_3$–$C_7$ cycloalkyl groups and carboxyl groups. Examples thereof are acetic acid, propionic acid, pivalic acid, chloroacetic acid, benzoic acid, terephthalic acid and phenylacetic acid. Particular preference is given to using acetic acid. In a further preferred embodiment of the process according to the invention, mixtures of organic acids can be used as well.

In a preferred embodiment of the process according to the invention, the aprotic organic solvent used is dioxane, ethyl acetate, propyl acetate, butyl acetate, chlorobenzene, acetonitrile or benzonitrile. Particular preference is given to using dioxane.

In a further preferred embodiment of the process according to the invention, mixtures of aprotic organic solvents can be used as well.

The process of the invention is preferably carried out using the organic acid in a ratio of 1:5 (v/v) to 5:1 (v/v) to the aprotic organic solvent, particular preference being given to a ratio of 1:2 (v/v) to 2:1 (v/v), and a ratio of 1:1 (v/v) is most preferred.

In a particularly preferred embodiment of the process according to the invention, the mixture of at least one organic acid and at least one aprotic organic solvent is a single-phase mixture.

The reactants used in the process of the invention are $C_6$–$C_{18}$ α,ω-dienes, e.g., 1,7-octadiene, 1,9-decadiene or 1,11-dodecadiene, which may optionally bear at least one substituent selectable from the group consisting of $C_1$–$C_6$ alkyl groups, e.g., methyl, ethyl, propyl or isopropyl groups, $C_6$–$C_{22}$ aryl groups, e.g., phenyl or naphthyl groups, $C_7$–$C_{24}$ arylalkyl groups, e.g., benzyl or phenylethyl groups, and halogens, e.g., chlorine or bromine. The reagent used is particularly preferably 1,7-octadiene, which the process of the invention converts into adipic acid.

In a further preferred embodiment of the process according to the invention, mixtures of $C_6$–$C_{18}$ α,ω-dienes can be used as well. The $C_4$–$C_{18}$ α,ω-dicarboxylic acid mixtures obtainable by the process of the invention are useful for polyester production, for example.

In a preferred embodiment of the process according to the invention, the transition metal catalyst of group VI is a tungstic acid, a tungstate or a tungsten complex. Particularly preferred tungstates are tungstates of oxidation states II, IV and VI, and most preference is given to using $Na_2WO_4$ or $(NH_4)_2WO_4$. A preferred tungsten complex is the peroxo complex $K_2WO_8$.

The hydrogen peroxide is preferably used in the process of the invention as a 5% to 50% (w/v) aqueous hydrogen peroxide solution, particularly preferably as a 30% to 50% (w/v) aqueous hydrogen peroxide solution.

Preferred compounds for releasing hydrogen peroxide under the reaction conditions are percarbonates, peroxyacids or perborates.

The process of the invention is customarily carried out using 9 to 20 equivalents of hydrogen peroxide based on the α,ω-diene used. Preference is given to using 10 to 13 equivalents.

The process of the invention is customarily carried out within the temperature range from about 40° C. to about 150° C., preferably a temperature that ranges from about 50° C. to about 120° C.

The process of the invention is particularly preferably carried out along a temperature profile. In this case, the temperature is maintained within the range from about 50°

C. to about 75° C. at the start of the process of the invention and is raised to a temperature that ranges from about 85° C. to about 120° C. after 30 to 90 minutes.

In a preferred form of the process according to the invention, the equivalents of hydrogen peroxide are added to the reaction mixture in two stages. Initially, 1.5 to 3.5 equivalents of hydrogen peroxide are added to the reaction mixture, based on the α,ω-diene used, while the temperature is maintained within the range of from about 50° C. to about 75° C. for 30 to 90 minutes. The temperature is then raised to a temperature that ranges from about 85° C. to about 120° C. and the remaining 5.5 to 18.5 equivalents of hydrogen peroxide are added. In a particularly preferred form of the process according to the invention, initially 2.5 equivalents of hydrogen peroxide are added at about 65° C. and the temperature is maintained for 60 min, and then the temperature is raised to about 95° C. and the remaining 9.5 equivalents of hydrogen peroxide are added.

The two-stage addition of hydrogen peroxide and the temperature profile lead to an increase in the selectivity with regard to the conversion into the desired α,ω-dicarboxylic acid.

The invention is further described in the following illustrative examples in which all parts and percentages are by weight unless otherwise indicated.

EXAMPLES

Example 1 (Inventive)

100 mmol of $H_2O_2$ in the form of a 30% (w/v) aqueous solution were added to 40 mmol 1,7-octadiene and 0.78 mmol of $(NH_4)_2WO_4$ in 50 ml of 1:1 (v/v) dioxane/acetic acid, and the mixture was heated to 65° C. with stirring. After 60 min the temperature was raised to 95° C. and a further 380 mmol of $H_2O_2$ were added. After 12 h the reaction was discontinued, manganese dioxide was added to catalytically decompose excess peroxide, and the solvent was distilled off.

The residue was crystallized to yield 5.55 g of adipic acid (95% of theory) as a white solid. The glutaric acid fraction was below 4%.

Example 2 (Comparative)

100 mmol of $H_2O_2$ in the form of a 30% (w/v) aqueous solution were added to 40 mmol 1,7-octadiene and 0.78 mmol of $(NH_4)_2WO_4$ in 50 ml of dioxane, and the mixture was heated to 65° C. with stirring. After 60 min the temperature was raised to 95° C. and a further 380 mmol of $H_2O_2$ were added. After 12 h the reaction was discontinued, manganese dioxide was added to catalytically decompose excess peroxide, and the solvent was distilled off.

The residue was crystallized to yield 2.97 g of adipic acid (51% of theory) as a white solid.

Example 3 (Comparative)

Comparative Example 2 was repeated using acetic acid instead of dioxane. After a reaction time of 24 h the yield was 3.96 g of adipic acid (75% of theory).

Example 4 (Comparative)

In a 100 ml two-neck flask 40 mmol of 1,7-octadiene, 0.78 mmol of $(NH_4)_2WO_4$ and 0.1 mmol of methyltrioctylammonium hydrogensulphate as phase transfer catalyst were dissolved in 40 ml of a 30% (w/v) hydrogen peroxide solution, maintained at 75° C. for 30 min with stirring and stirred at 95° C. for 47 h. After the solvent was distilled off, the residue was made to yield 4.40 g of a white solid which contained 3.78 g of adipic acid (65% of theory) as well as 0.62 g of glutaric acid (adipic acid/glutaric acid ratio 5:1).

Although the present invention has been described in detail with reference to certain preferred versions thereof, other variations are possible. Therefore, the spirit and scope of the appended claims should not be limited to the description of the versions contained therein.

What is claimed is:

1. A process for preparing an optionally-substituted aliphatic $C_4$–$C_{18}$ α,ω-dicarboxylic acid comprising the step of oxidizing (a) a member selected from the group consisting of unsubstituted $C_6$–$C_{20}$ α,ω-dienes and substituted $C_6$–$C_{20}$ α,ω-dienes with (b) a member selected from the group consisting of hydrogen peroxide and compounds which release hydrogen peroxide under the reaction conditions:

wherein the reaction is carried out in the presence of a transition metal catalyst of group VI and in the presence of a mixture comprising at least one organic acid and at least one aprotic organic solvent comprising a member selected from the group consisting of dioxane, ethyl acetate, propyl acetate, butyl acetate, chlorobenzene, acetonitrile and benzonitrile solvents, wherein oxidation is carried out along a temperature profile that is maintained within a range from about 50° C. to about 75° C. at the start of the process and is raised to a temperature ranging from about 85° C. to about 120° C.

2. The process of claim 1, wherein the mixing ratio of at least one organic acid and at least one aprotic solvent is from 1:5 (v/v) to about 5:1 (v/v).

3. The process of claim 1, wherein the mixing ratio of at least one organic acid and at least one aprotic solvent is from about 1:2 (v/v) to about 2:1 (v/v).

4. The process of claim 1, wherein the mixing ratio of at least one organic acid and at least one aprotic solvent is about 1:1 (v/v).

5. The process of claim 1, wherein the $C_6$–$C_{20}$ α,ω-diene reactants bear at least one substituent selected from the group consisting of $C_1$–$C_6$ alkyl groups, $C_6$–$C_{22}$ aryl groups, $C_7$–$C_{24}$ arylalkyl groups and halogens.

6. The process of claim 1, wherein the transition metal catalyst of group VI is selected from the group consisting of tungstic acid, fungstate and tungsten complexes.

7. The process of claim 1, wherein from about 9 to about 20 equivalents of hydrogen peroxide are used, based on the $C_6$–$C_{20}$ α,ω-diene used.

8. The process of claim 1, wherein from about 10 to about 13 equivalents of hydrogen peroxide are used, based on the $C_6$–$C_{20}$ α,ω-diene used.

9. A process for preparing an optionally-substituted aliphatic $C_4$–$C_{18}$ α,ω-dicarboxylic acid comprising the step of oxidizing (a) a member selected from the group consisting of unsubstituted $C_6$–$C_{20}$ α,ω-diene and substituted $C_6$–$C_{20}$ α,ω-dienes with (b) a member selected from the group consisting of hydrogen peroxide and compounds which release hydrogen peroxide under the reaction conditions:

wherein the reaction is carried out in the presence of a transition metal catalyst of group VI and in the presence of a mixture comprising at least one organic acid and at least one aprotic organic solvent comprising a member selected from the group consisting of dioxane, ethyl acetate, propyl acetate, chlorobenzene, acetonitrile and benzonitrile solvents, wherein the oxidation is carried out along a temperature profile the is maintained within a range from about 50° C. to about 75° C. at the start of the process and is raised to a temperature ranging from about 85° C. to about 120° C. and the equivalents of hydrogen peroxide are added in two stages.

10. A process for preparing an optionally-substituted aliphatic $C_4$–$C_{18}$ α,ω-dicarboxylic acid comprising the step of oxidizing (a) a member selected from the group consisting of unsubstituted $C_6$–$C_{20}$ α,ω-dienes and substituted $C_6$–$C_{20}$ α,ω-dienes with (b) a member selected from the group consisting of hydrogen peroxide and compounds which release hydrogen peroxide under the reaction conditions:

wherein the reaction is carried out in the presence of a transition metal catalyst of group VI and in the presence of a mixture comprising at least one organic acid and at least one aprotic organic solvent comprising a member selected from the group consisting of dioxane, ethyl acetate, propyl acetate, butyl acetate, chlorobenzene, acetonitrile and benzonitrile solvents, and wherein the 1.7-octadiene is oxidized to form adipic acid.

* * * * *